United States Patent [19]

Rasmussen et al.

[11] Patent Number: 4,639,286

[45] Date of Patent: Jan. 27, 1987

[54] CURABLE COMPOSITIONS CONTAINING AZLACTONE-FUNCTIONAL COMPOUNDS

[75] Inventors: Jerald K. Rasmussen, Stillwater; Steven M. Heilmann, North St. Paul; Frederick J. Palensky, St. Paul, all of Minn.

[73] Assignee: Minnesota Mining and Manufacturing Company, St. Paul, Minn.

[21] Appl. No.: 641,924

[22] Filed: Aug. 17, 1984

Related U.S. Application Data

[62] Division of Ser. No. 424,500, Sep. 27, 1984, Pat. No. 4,485,236.

[51] Int. Cl.$^4$ .......................... C09J 3/14; C09J 5/04; C08G 69/42
[52] U.S. Cl. ................................ 156/307.3; 156/310; 156/331.1; 528/354; 528/363; 528/364; 528/422; 528/423; 544/63; 544/69
[58] Field of Search ............... 528/354, 363, 364, 374, 528/422, 423, 424; 156/285, 307.3, 310, 331.5, 331.1; 544/63, 69; 525/419, 421, 540

[56] References Cited

U.S. PATENT DOCUMENTS

| | | | |
|---|---|---|---|
| 4,092,298 | 5/1978 | Humbert et al. | 260/75 |
| 4,153,785 | 5/1979 | Schulz et al. | 528/354 |
| 4,291,152 | 9/1981 | Inata et al. | 528/289 |
| 4,304,705 | 12/1981 | Heilmann et al. | 428/500 X |
| 4,474,942 | 10/1984 | Sano et al. | 528/363 |

FOREIGN PATENT DOCUMENTS

| | | |
|---|---|---|
| 2516978 | 10/1976 | Fed. Rep. of Germany . |
| 1121418 | 7/1968 | United Kingdom ............ 526/260 |

OTHER PUBLICATIONS

Schildknecht, "Polymerizations in Bulk", in Polymer Processes, Schildknecht (ed.), p. 31, Interscience Publishers, Inc., N.Y. (1956).
Drey, et al, Chemical Abstracts, vol. 97 (1982) 198543y.
March, Advanced Organic Chemistry, McGraw-Hill Book Co., New York, (1977) pp. 727 & 728.
Hubner, K., Kollinsky, F., Markert, G., and Pennewiss, H., *Angew. Makromol. Chem.*, 11, 109 (1970).
Taylor, L. D. and Platt, T. E., *J. Polym. Sci., Polym. Letters Edit.*, 7, 597 (1969).
Cleaver, C. S. and Pratt, B. C., *J. Amer. Chem. Soc.*, 77, 1541, 1544 (1955).
Ueda, M., et al., *J. Polym. Sci.: Polym. Chem. Ed.*, 16, 155 (1978).
Iwakura, Y., Toda, F., and Torii, Y., *Tetrahedron*, 23, 3363 (1967).

*Primary Examiner*—Joseph L. Schofer
*Assistant Examiner*—F. M. Teskin
*Attorney, Agent, or Firm*—Donald M. Sell; James A. Smith; Lorraine R. Sherman

[57] ABSTRACT

Azlactone-functional compounds, which are liquid above 20° C., and their method of preparation from alkenyl azlactones and nucleophilic group-substituted compounds are disclosed. The azlactone-functional compounds of the invention cure in the presence of nucleophilic chain-extending or crosslinking agents to form linear or crosslinked polyamide resin systems.

14 Claims, No Drawings

CURABLE COMPOSITIONS CONTAINING AZLACTONE-FUNCTIONAL COMPOUNDS

This is a division of application Ser. No. 424,500 filed Sept. 27, 1984, now U.S. Pat. No. 4,485,236.

TECHNICAL FIELD

This invention relates to azlactone compounds useful for the preparation of polyamide resins and to a process for their synthesis. The invention further relates to curable compositions containing the azlactone compounds, the cured resins prepared therefrom, and a process therefor.

BACKGROUND ART

The chemistry of azlactones has received considerable attention in the literature, mainly as it relates to amino acid and peptide chemistry. Azlactones are known to react with a variety of nucleophiles (e.g., alcohols, amines, mercaptans) by a ring-opening reaction to produce compounds containing ester, amide, or thioloester linkages. By contrast, bis(azlactones) are less well known, particularly those of the 2,2'-bis(2-oxazolin-5-one) class.

C. S. Cleaver and B. C. Pratt, *J. Amer. Chem. Soc.*, 77, 1541, 1544 (1955), conducted the first systematic studies on the synthesis and characterization of bis(azlactones) having aromatic and hydrocarbon linkages to the 2-positions of the two azlactones. These compounds were used to prepare a new series of polyamides containing a regular arrangement of "head-to-tail" and "tail-to-tail" amide groups. Other investigators, e.g., M. Ueda, et al., *J. Polym. Sci.:Polym. Chem. Ed.*, 16, 155 (1978), have expanded upon this method of polyamide synthesis. Diefenback, et al., Ger Offen. No. 2,516,978, Oct. 28, 1976, (*Chem. Abstr.*, 86, 3112t, 1977), describe the use of compounds containing two azlactone rings linked by a tetramethylene group as a crosslinking agent for high solids and powder coatings. Humbert, et al., U.S. Pat. No. 4,092,298, teach the use of bis(azlactones), wherein the linking group is a hydrocarbon or halo-substituted hydrocarbon group, as novel crosslinking agents for hydroxy-containing polymeric powder coating compositions. In addition, Inata, et al., U.S. Pat. No. 4,291,152, teach the use of bis(azlactones), wherein the linking group between the azlactone rings may be

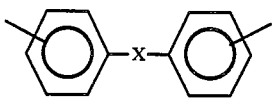

where X is O, S, CO, or SO$_2$, for the purpose of chain-extending linear, hydroxy-terminated polyesters.

β-Hetero(nitrogen or sulfur)-substituted ethylene groups are not known in the art as linking groups between the 2-positions of azlactones, and the use of bis- and poly(azlactone) compounds, with these linking groups, suitable for the preparation of thermoplastic and thermosetting resins has not been disclosed.

Further, the preparation of bis(azlactones) in the prior art is generally accomplished via the Schotten-Baumann reaction of a dicarboxylic acid dichloride with an α-amino acid, followed by a dehydrative ring-closure reaction. Overall yields from this reaction sequence are generally poor, and the latter step is fraught with difficulties (see previously cited Cleaver and Pratt article). In addition, all known examples of bis(azlactones) are crystalline solids, often exhibiting high melting points and corresponding limited solubilities in the types of materials useful for the preparation of curable resins.

DISCLOSURE OF THE INVENTION

The present invention provides a new class of azlactone-functional compounds that are liquid at temperatures above 50° C., preferably above 20° C., are soluble in curable resin systems and are useful for the preparation of polyamide resins. The azlactone-functional compounds of the invention have the general formula

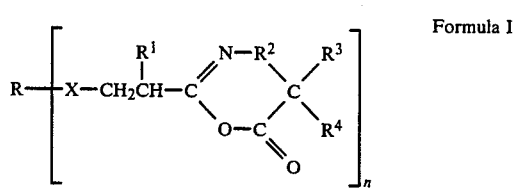

Formula I wherein

R$^1$ is hydrogen, chlorine or a methyl group;

R$^2$ is a single bond or a methylene or ethylene group, the last two of which can be substituted by alkyl groups having 1 to 6 carbon atoms or phenyl groups;

R$^3$ and R$^4$ are independently an alkyl or cycloalkyl group having 1 to 12 carbon atoms, an aryl or aralkyl group having 6 to 12 carbon atoms, or R$^3$ and R$^4$ taken together with the carbon atom to which they are attached form a 5- to 12-membered carbocyclic ring;

X is a nucleophilic group selected from $$\begin{matrix} R^5 \\ | \\ -N- \end{matrix}$$

and —S—, in which R$^5$ is a hydrocarbyl group selected from (1) an alkyl or cycloalkyl group having 1 to 18 carbon atoms, or (2) an aryl or aralkyl group having 6 to 12 carbon atoms;

R is an organic group that has a valence of n and is the residue of a nucleophilic group-substituted compound, (HX)$_n$R, in which X is defined above, the residue having a molecular weight up to 20,000, preferably selected from mono- and polyvalent hydrocarbyl (i.e., aliphatic and aryl compounds having 2 to 20 carbon atoms and optionally one to four catenary heteroatoms of oxygen, nitrogen or sulfur, e.g., piperazine, furan, thiophene), polyoxyalkylene, polyester, polyolefin, polyacrylate, and polysiloxane residues that can optionally all be further substituted by at least one non-nucleophilic group such as cyano, halo, ester, ether, keto, nitro, silyl, sulfide (the carbon-containing groups having up to 10 carbon atoms), and nucleophilic groups including secondary amino groups, hydroxyl groups or mercapto groups; and n is an integer having a value of one to six.

Optionally, R$^3$, R$^4$, and R$^5$ can be hydrocarbons or they can be substituted by any group that does not react with the azlactone ring, such as cyano, halo, ester, alkoxy, keto, nitro, silyl, and sulfide (the carbon-containing groups having up to 10 carbon atoms).

The present invention also provides a process for the production of the azlactone-functional compounds of Formula I by a Michael Reaction (also called Michael Addition) wherein amino or thiol group-substituted nucleophilic compounds add to alkenyl azlactone compounds, the method comprising the steps:

(1) admixing
(a) one to n gram moles of at least one alkenyl azlactone having the formula.

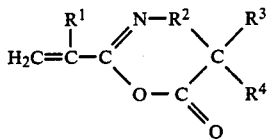

Formula II wherein $R^1$, $R^2$, $R^3$, and $R^4$ are defined for Formula I with
(b) one gram mole of at least one nucleophilic group-substituted compound having the formula.

$(HX)_nR$            Formula III wherein X, R, and n are defined for Formula I, with the proviso that when X is —S—, then a catalytic amount (from 0.001 to 5 percent by weight, preferably from 0.01 to 1.0 percent by weight based on total weight of alkenyl azlactone of an acid, preferably a Bronsted acid having a $pK_a$ less than 5.0 is present;

(2) allowing the mixture to react at 0° to 100° C. until complete as determined by infrared (IR) spectroscopy.

The present invention further provides polyamide resins as shown in Formula IV having repeating units having the structure

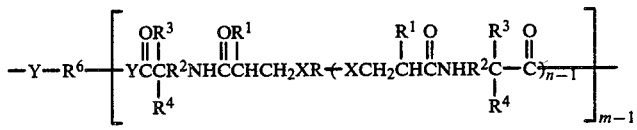

Formula IV wherein
$R^1$, $R^2$, $R^3$, $R^4$, R, n, and X are the same as defined for Formula I;

$R^6$ is an organic group that has a valence of m and is the residue of a nucleophilic group-substituted chain-extending or crosslinking agent, $R^6(YH)_m$, having a molecular weight up to 500,000, preferably selected from mono- and polyvalent organic groups (i.e., aliphatic and aryl groups having 2 to 20 carbon atoms and optionally one to four catenary heteroatoms selected from oxygen, nitrogen, and sulfur, e.g., piperazine, furan, thiophene), polyoxyalkylene, polyester, polyolefin, polyacrylate, and polysiloxane groups that can optionally all be further substituted by at least one non-nucleophilic group such as cyano, halo, ester, ether, keto, nitro, silyl, and sulfide, wherein Y is —O—, —X—, or

in which $R^7$ is hydrogen or lower alkyl group having one to four carbon atoms, and m is an integer of 1 to 20,000.

As used in the present application: "catenary" means in the backbone or main chain, as opposed to being in a pendant group.

DETAILED DESCRIPTION OF THE INVENTION

Suitable alkenyl azlactones for use in the preparation of the azlactone-functional compounds of the invention are well-known and their synthesis has been fully discussed in the literature by:

(1) Y. Iwakura, F. Toda and Y. Torii, *Tetrahedron*, 23, 3363 (1967);
(2) K. Hubner, F. Kollinsky, G. Markert and H. Pennewiss, *Angew. Makromol.Chem.*, 11, 109 (1970);
(3) L. D. Taylor and T. E. Platt, *J. Polym. Sci., Polym. Letters Edit.*, 7, 597 (1969);

particularly with regard to the 5-membered rings, the 2-alkenyl-2-oxazolin-5-ones.

Typically, an amino acid is reacted with an acryloylating agent (e.g., (meth)acryloyl chloride or (meth)acrylic anhydride) in the presence of a base (e.g., aqueous sodium hydroxide) to produce an acryloylated amino acid. Cyclization to the azlactone is then accomplished in the presence of a dehydrating agent (e.g., acetic anhydride, ethyl chloroformate or dicyclohexylcarbodiimide). In analogous fashion, the higher membered analogues may be prepared and used for preparation of the compounds of the present invention. Due to the greater stability of the 5-membered ring azlactones, these compounds are preferred. Most preferred are those in which $R^3$ and $R^4$ independently represent hydrocarbon radicals of from 1 to about 12 carbon atoms.

Examples of alkenyl azlactones (Formula II) include 2-ethenyl-4-methyl-4-phenyl-2-oxazolin-5-one, 2-ethenyl-4,4-dimethyl-2-oxazolin-5-one, 2-isopropenyl-4,4-dimethyl-2-oxazolin-5-one. Others are disclosed in assignee's pending patent application U.S. Ser. No. 316,234, filed Oct. 29, 1981.

Nucleophilic group-substituted compounds of Formula III which can be caused to react with the alkenyl azlactone compounds of Formula II in accordance with the process aspect of the invention to prepare the azlactone-functional compounds (Formula I) of the invention vary widely within the scope of the invention and include (1) mercaptans and (2) secondary amines, both of which may be monofunctional or polyfunctional. These mercaptan- and secondary amine-functional compounds may have low or high molecular weights from 34, in the extreme case of hydrogen sulfide, to, for example, about 20,000 in the case of polymeric mercaptans or secondary amines. These compounds are often hydrocarbyl substituted but may contain other substituents either as pendant or catenary (in the backbone) units such as cyano, halo, ester, ether, keto, nitro, sulfide or silyl groups, with ester and ether units being common and preferred. Reactive substituting groups to be avoided are primary amino groups. Examples of nucleophilic group-substituted compounds of Formula III useful for the preparation of the azlactone-functional compounds of the invention include the (1) mercapto- and polymercapto-functional compounds such as hydrogen sulfide; aliphatic mercaptans such as ethanethiol, lauryl mercaptan, octadecyl mercaptan, 1,2- ethanedithiol, 1-butanethiol, 1,4-butanedithiol, 1,3,5-pentanetrithiol, 1,12-dodecanedithiol, 2,2'-oxybis(ethanethiol), 4,4'-oxybis(butanethiol), and 4,4'-thiabis(butanethiol); esters of thioaliphatic acids such as 1,2-ethanediyl bis(mercaptoacetate), 1,4-butanediyl bis(mercaptoacetate), 1,2-ethanediyl bis(3-mercaptopropionate), trimethylolpropane tris(3-mercaptopropionate), trimethylolpropane tris(mercaptoacetate), 1,6-hexanediyl bis(3-mercaptopropionate), 1,2,3-propanetriyl tris(mercaptoacetate), 2-methylthio-1,3-propanediyl bis(3-mercaptopropionate), 2-chloro-1,3-propanediyl bis[thio(4-mercaptobutyrate)], pentaerythritol tetra(mercaptoacetate), and 1,2,3,4,5,6-hexanehexayl hexa(mercaptoacetate); aryl and aralkyl mercaptans such as benzenethiol, 1,4-benzenedithiol, oxydi(benzylmercaptan), and 3,4-toluenedithiol; the mercapto-functional compounds such as the mercaptoacetate and mercaptopropionate esters of polymeric alcohols such as the polyoxyalkylenepolyols, polyesterpolyols, polylactonepolyols, polyolefinpolyols, and the polysiloxane polyols, i.e., the di- and tri-mercaptopropionate esters of poly(oxyethylene)diols and triols, the poly(oxypropylene) diols and triols, and the polycaprolactonediols and triols; and (2) the secondary amino- and poly(secondary amino)-functional compounds such as dimethylamine, dibutylamine, didodecylamine, N,N'-dimethyl-1,2-ethanediamine, N,N'-dimethyl-1,6-hexanediamine, $N^1,N^2$-dimethyl-$N^3$-propyl-1,2,3-propanetriamine, N,N'-diphenyl-1,4-benzenediamine, N,N'-dimethyl-1,3-benzenediamine, N-(2-chlorophenyl)-N'-methyl-1,4-butanediamine, 3-(cyclohexylamino)pyrrolidine, 4,4'-trimethylenedipiperidine, $N^1,N^{11}$-diphenyl-3,6,9-triazaundecane-1,11-diamine, N,N'-bis(2-cyanoethyl)-1,5-(3-oxapentane)diamine, 2,5-dimethylpiperazine, and the cyanoethylated derivatives of polyoxyalkylene polyamines such as those available from Jefferson Chemical Co., Inc., under the tradename Jeffamine ® (CD-series).

While the azlactone-functional compounds prepared from compounds such as those listed above having more than one nucleophilic group constitute a preferred aspect of this invention, it should be obvious that monoazlactone-functional materials may also be prepared and are within the scope of the invention. Such monoazlactone-functional compounds are useful, for example, as reactive diluents for the multiazlactone-functional compounds and as components of other curable resin systems, or as curable materials in their own right. For example, Michael Reaction of 2-mercaptoethanol with 2-ethenyl-4,4-dimethyl-2-oxazolin-5-one rapidly produces hydroxy-functional azlactone V, which upon heating or upon long-term reaction at room temperature produces linear polyesteramide VI via self-condensation.

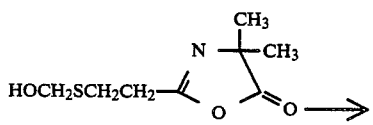

V

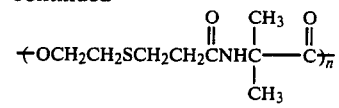

VI

Similarly, use of a mercaptodiol produces a selfcrosslinkable resin. In analogous fashion, reaction of mercaptofunctional silanes, such as 3-mercaptopropyltrimethoxysilane, with alkenyl azlactones produces azlactone-functional silane coupling agents and crosslinking agents.

The novel azlactone-functional resins of general Formula I of this invention are prepared by the Michael Reaction of nucleophilic group-substituted compounds of Formula III with alkenyl azlactones of Formula II. In general, Michael Reaction is accomplished by simply mixing the two components at room temperature. A mild exotherm may occur, which can be mediated if desired by the use of a cooling bath. The progress of the reaction is conveniently monitored by infrared spectroscopy, observing the disappearance of the C=C double bond absorption of the alkenyl azlactone. Optionally, the process may also be carried out in a solvent as a nonreactive diluent for the reaction. Nonreactive solvents are the common organic solvents, including the aliphatic or aromatic hydrocarbons such as pentane, hexane, benzene, and toluene; chlorinated solvents such as dichloromethane, chloroform, and carbon tetrachloride; ester solvents such as ethyl acetate; ketones such as acetone and methyl ethyl ketone; ethers such as diethyl ether and tetrahydrofuran; and other nonreactive solvents.

With amino-functional reactants of Formula III, the Michael Reaction generally occurs only slowly at ambient temperatures and, therefore, may require heating to ensure complete reaction. For example, highly hindered secondary amines such as the Jeffamine ® CD-series polyamines, which have secondary amino-functionality of the following structure

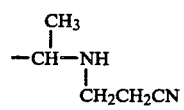

require heating at 50°-70° C. for 12 to 24 hours.

Michael Reaction of mercaptan-functional compounds of Formula III with alkenyl azlactones of Formula II takes place rapidly at room temperature in the presence of an acidic catalyst. Basic catalysts, in general, lead to ring-opening reaction products rather than the desired Michael Reaction. Preferred catalysts are strong protonic acids or Brønsted acids including organic acids such as alkyl and arylsulfonic acids and trifluoroacetic acid; inorganic acids such as sulfuric acid, phosphoric acid, hydrochloric acid, and perchloric acid; and Lewis acids such as boron trifluoride, titanium tetrachloride, aluminum trichloride, and phosphorous pentachloride. Most preferred are the Brønsted acids. The commercially obtained esters of mercapto-functional acids often contain sufficient amounts of acidic catalytic material (as an unremoved impurity resulting from their synthesis) to be used in preparing the compounds of the invention without the addition of additional acid catalyst. Generally, a catalyst concentration of 0.001 to 5.0 and preferably about 0.01 to 1 percent by weight based upon the total weight of alkenyl azlactone is sufficient to ensure rapid reaction.

Illustrative of the azlactone-functional compounds of the invention, Formula I, are
1,2-bis[2-(4,4-dimethyl-2-oxazolin-5-one-2-yl)ethylthio]ethane
1,5-bis[2-(4,4-dimethyl-2-oxazolin-5-one-2-yl)ethylthio]3-oxapentane
1,10-bis[2-(4,4-dimethyl-2-oxazolin-5-one-2-yl)ethylthio]4,7-dioxadecane-3,8-dione
1,1,1-tris[[2-[2-(4,4-dimethyl-2-oxazolin-5-one-2-yl)ethylthio]ethylcarbonyloxymethyl]]propane
1,5-bis[2-(4,4-dimethyl-2-oxazolin-5-one-2-yl)-2-methylethylthio]-3-oxapentane
1,5-bis[2-(4-methyl-4-nonyl-2-oxazolin-5-one-2-yl)-ethylthio]-3-oxapentane
1,5-bis[2-(4,4-dimethyl-2-oxazolin-5-one-2-yl)ethylthio]-3-thiapentane
1,5-bis[2-(4,4-dimethyl-2-oxazolin-5-one-2-yl)ethyl-N-methylamino]-3-oxapentane
1-butylamino-2-[2-(4,4-dimethyl-2-oxazolin-5-one-2-yl)ethylthio]ethane
1-mercapto-2-[2-(4,4-dimethyl-2-oxazolin-5-one-2-yl)ethylthio]ethane
1-hydroxy-2-[2-(4,4-dimethyl-2-oxazolin-5-one-2-yl)ethylthio]ethane
1-trimethoxysilyl-3-[2-(4,4-dimethyl-2-oxazolin-5-one-2-yl)ethylthio]propane
1-phenylamino-5-[2-(4,4-dimethyl-2-oxazolin-5-one-2-yl)ethylthio]-3-oxapentane
α,ω-bis[5-(4,4-dimethyl-2-oxazolin-5-one-2-yl)-3-aza-3-(2-cyanoethyl)-2-methylpentyl]poly(oxypropylene)
1,8-bis[2-(4,4-dimethyl-2-oxazolin-5-one-2-yl)ethylthio]-3,6-dioxaoctane-2,7-dione
1,1,1-tris[2-[2-(4,4-dimethyl-2-oxazolin-5-one-2-yl)ethylthio]methylcarbonyloxymethyl]propane
1-trimethylsilyl-3-[2-(4,4-dimethyl-2-oxazolin-5-one-2-yl)ethylthio]propane.

Being azlactone-functional, the compounds of the invention are susceptible to ring-opening reactions with nucleophilic group-functional compounds such as alcohols, polyols, amines, and polyamines. The electrophilicity of the azlactone group is such that these resins display reactivity which is intermediate between that of epoxies and that of isocyanates. That is, the azlactones are more reactive towards nucleophiles than are epoxy resins, but are much more controllable in their reactivity than are isocyanates and are not so susceptible to contamination by water. This feature makes these resins desirable for the preparation of curable resins and adhesives. In this respect, a particular feature of the novel azlactone-functional resins of the present invention is their normally liquid or fluid nature at ambient or near ambient temperatures. This feature ensures compatibility with the typical materials and resins useful as curatives or coreactants.

Nucleophilic group-functional chain-extending or crosslinking agents, $R^6$-(-YH)$_m$, defined under Formula IV, include not only the nucleophilic group-functional compounds R—XH)$_n$, defined under Formula III that are useful for preparation of the compounds of Formula I, but also other bis- and poly-nucleophilic group-substituted compounds having molecular weights up to 500,000 which would not be useful for the preparation of the compounds of Formula I. Examples of such compounds include simple polyamines such as ethylenediamine, 1,4-butanediamine, benzenediamines, 1,4-cyclohexanediamine, 1,6-hexanediamine, N,N'-bis(3-aminopropyl)piperazine, diethylenetriamine, triethylenetetramine, and tetraethylenepentamine; simple polyols such as ethylene glycol, diethyleneglycol, 1,6-hexanediol, 1,4-cyclohexanedimethanol, glycerol, trimethylolpropane, pentaerythritol, and dipentaerythritol; amino alcohols such as 2-aminoethanol, 4-aminobutanol, 2-amino-2-methyl-1,3-propanediol, and N-hydroxyethylpiperazine; polyether polyols such as polyethyleneglycol, polypropyleneglycol, and polytetramethyleneglycol; polyester polyols such as polycaprolactone polyols, and poly(neopentyl adipate) polyols; polyoxyalkylene polyamines such as the polyethylene- and polypropyleneoxide based mono- and polyamines available from Jefferson Chemical Co., Inc., a subsidiary of Texaco, Inc., under the tradename Jeffamine ®; hydroxy- and amino-functional derivatives of polymerized fatty acids, more commonly referred to as "dimer" or "trimer" acid derivatives, such as those sold commercially under the trade designation Kemamine ® (Humko Sheffield Chemical); hydroxy- or amino-functional olefin polymers and copolymers, such as hydroxy-terminated polybutadienes, amine-terminated butadiene, acrylonitrile copolymers (B. F. Goodrich's HYCAR ® ATBN); primary and secondary amino-functional polyamides such as those useful as epoxy curing agents (e.g. Emerez ® reactive polyamide resins from Emery Industries, Inc.); polyethyleneimines; polyvinyl alcohol and other hydrolyzed or partially hydrolyzed vinyl acetate homo- and interpolymers; and polysiloxane polyols such as those described in U.S. Pat. Nos. 4,098,742; 3,886,865; 3,577,264; and 4,013,698. A particular class of materials useful for preparation of the polyamides of Formula IV of the present invention is a series of polyamides of polyethers of the general structure:

wherein $R^8$ is the residue of a mono- or polyfunctional carboxylic acid having at least one active hydrogen removed therefrom, $R^9$ is a polyether radical corresponding to a polyether polyamine having a molecular weight of from about 200 to about 10,000, and a and b are independently integers from 1 to about 4. These polyamines are conveniently prepared by standard condensation techniques from the appropriate organic acid (or suitable derivative) and excess polyether polyamine such as those described in U.S. Pat. Nos 4,107,061 and 3,257,342, incorporated herein by reference.

The process for preparing the novel polyamides of the invention, Formula IV, involves generally admixing 0.8 to 1.2 equivalents, based on functionality, of the azlactone-functional compounds of Formula I with the nucleophilic group-substituted compounds, R(XH)$_n$ or $R^6$(YH)$_m$, with appropriate stirring, at a temperature of about 0° C. to 50° C. and under atmospheric pressure, and optionally in the presence of a nonreactive organic solvent or water as a diluent. Because the azlactone-functional compounds are liquid or low temperature melting solids, i.e. have a melting point of less than about 50° C., they are generally easily mixed with the nucleophilic compound in simple stirring equipment, therefore making the use of solvent unnecessary. The two reactants can be charged into the reaction vessel in any order. When the nucleophilic compound is amine-functional, particularly primary amine-functional, the reaction to produce the polyamides of Formula IV proceeds rapidly so that, if desired, the reactants can be extruded or charged into a mold to provide a desired product shape. When the nucleophilic compound is alcohol-functional, reaction at room temperature is sluggish in the absence of a catalyst. When it is desired to accomplish reaction at or near room temperature, Brønsted (i.e. protonic) and Lewis acid catalysts are preferred. Weakly basic catalysts such as triethylamine, pyridine, 4-dimethylaminopyridine, and diazabicyclooctane, as well as strongly basic catalysts such as tetrabutylammonium hydroxide, alkali metal hydroxides, and alkali metal alkoxides may also be used as catalysts for the reaction with polyols, particularly in conjunction with the use of elevated temperatures. From about 0.001 to 5 percent, preferably from about 0.01 to 1 percent, by weight of catalyst based upon the azlactone-functional compound is used for promoting the reaction. Although the reactivity of the nucleophilic compound (as in the case of amine reactants) or the type or level of catalyst (as in the case of alcohol reactants) can be chosen such that the major portion of the reaction can be completed within about 5 minutes without the application of external heating, it may be desirable to heat the product at elevated temperatures up to about 300° C. for an hour or more to further advance the degree of polymerization or increase the degree of cure in the resultant polyamide of Formula IV.

As should be apparent to one skilled in the art, reaction of azlactone-functional compounds, Formula I, with chain-extending or crosslinking agents, $R^6(YH)_m$, in which the value of either or both of m or n is greater than 2 will result in a crosslinked or thermoset polyamide resin system, Formula IV. This aspect is especially useful in the utilization of compounds of Formula I as components of curable resins, as for example as one- or two-part adhesives or coatings, and for the molding of shaped articles. In this aspect of the invention, it should also be apparent that the rate of crosslinking or curing is a function of the nature of the nucleophilic group-substituted compound being reacted with the compound of Formula I, as well as the parameters of catalyst and temperature as discussed above. These factors are important in adjusting the reaction rate to suit the desired application. Furthermore, it should be apparent that reactions conducted with components in which both m and n are equal to 2, will result in linear thermoplastic polyamides. In this aspect of the invention, where it is often desirable to achieve the highest possible molecular weight in the polyamide so as to maximize polymer properties, it is desirable to conduct the polymerization reaction at elevated temperatures, i.e. at temperatures high enough above the melt transition of the resultant polyamide to maintain sufficient fluidity to ensure diffusion and efficient reaction between the functional groups. In all aspects of this invention related to the preparation of polyamides of Formula IV, it is contemplated as being within the scope of the invention to utilize a combination of two or more nucleophilic group-substituted compounds for reaction with the compounds of Formula I. This also provides an additional parameter by which the rate of the polymerization or curing reaction can be controlled.

The compositions of the invention to be reacted to form the polyamides of the invention may, if desired, include such additives as antioxidants, accelerators, dyes, inhibitors, flame retardants, thickeners, thixotropic agents, surface active agents, viscosity modifiers, plasticizers, and tackifiers; all are within the scope of this invention. Such additives are usually preblended with the nucleophilic compound prior to the addition of the azlactone-functional compounds. Fillers also may be included in the composition such as natural and synthetic resins, carbon black, glass fibers, wood flour, clay, silica, alumina, carbonates, oxides, silicates, glass flakes and beads, borates, and talc. These may be used up to 500 parts by weight or more per 100 parts by weight of combined nucleophilic and azlactone-functional compound and preferably about 10 to about 250 parts on the same basis.

The azlactone-functional compounds of Formula I of the present invention find utility as monomers or prepolymers for thermoplastic and thermosetting polyamide resins of Formula IV that are useful as adhesives, coatings, molded articles, foamed articles and the like.

A composition of the invention is typically stored in two parts prior to introduction for use as an adhesive, with the reactive azlactone-functional compound being present in one part, and the reactive nucleophilic group-substituted compound in the second part. If the nucleophilic compound is hydroxy-functional, an acid catalyst is present in the second part to provide an effective reaction rate. As is well known in the art (see, for example, U.S. Pat. Nos. 2,932,385, 2,967,795, 2,756,875, 3,074,544, 3,087,606, and 4,060,583), two-part compositions may conveniently be stored until use in separate compartments of a multicompartment unitary package. The compartments are typically separated by a membrane or seam which may be ruptured to allow mixing of the separate parts immediately prior to use.

Objects and advantages of this invention are further illustrated by the following examples, but the particular materials and amounts thereof recited in these examples, as well as other conditions and details, should not be construed to unduly limit this invention. In all cases, unless otherwise noted, all parts and percentages are by weight.

EXAMPLE 1

A round-bottomed flask equipped with a mechanical stirrer and a dropping funnel was charged with 33.8 g 2-ethenyl-4,4-dimethyl-2-oxazolin-5-one (0.24 mole). To this was added in one portion, with stirring, 31.0 g trimethylolpropane tris(thioglycolate) (Evans Chemetics, Inc., mercaptan equivalent weight 129.2, 0.24 equivalents). A mild exotherm ensued, therefore the flask was immersed in a cold (approximately 15° C.) water bath. After one hour, the cooling bath was removed. Stirring was continued at room temperature until analysis of the reaction mixture by infrared spectroscopy indicated complete disappearance of the azlactone carbon-carbon double bond absorption. The resultant tris(azlactone) was identified by spectroscopic analysis.

EXAMPLES 2–9

Using a procedure similar to that of Example 1, a number of other azlactone-functional resins were prepared from mercaptans and alkenyl azlactones as shown in Table I. Infrared and NMR spectral analyses were utilized in all cases to verify formation of azlactone-functional products.

TABLE I

| Example | Azlactone* | Mercaptan |
|---|---|---|
| 2 | A | ethyleneglycol bis(mercaptopropionate) |
| 3 | A | 1,2-ethanedithiol[a] |
| 4 | A | 2-mercaptoethanol |
| 5 | A | 3-mercaptopropyltrimethoxysilane |
| 6 | A | bis(2-mercaptoethyl)ether |
| 7 | A | trimethylolpropane tris(mercaptopropionate) |
| 8 | B | ethyleneglycol bis(thioglycolate) |
| 9 | C | ethyleneglycol bis(thioglycolate) |

*A 2-Ethenyl-4,4-dimethyl-2-oxazolin-5-one
B 2-Isopropenyl-4,4-dimethyl-2-oxazolin-5-one
C 2-Ethenyl-4-methyl-4-n-nonyl-2-oxazolin-5-one
[a]The adduct was a low melting solid.

EXAMPLE 10

A reaction vessel was charged with 4.8 g 2-ethenyl-4,4-dimethyl-2-oxazolin-5-one (34.6 mmoles) and 37.1 g Jeffamine® CD-2000 (Jefferson Chemical Co., Inc., poly(oxypropylene diamine), approximate molecular formula $$NCCH_2CH_2NH \text{---} (\overset{CH_3}{\underset{|}{C}}HCH_2O)_{33} \text{---} CH_2\overset{CH_3}{\underset{|}{C}}HNHCH_2CH_2CN,$$

equivalent weight 1073, 34.6 mequiv.), sealed, and agitated at room temperature. After 48 hours, infrared analysis indicated little or no reaction had occurred. Therefore, the vessel and its contents were placed in an oven at 70° C. After 24 hours, IR analysis indicated complete conversion to the bis(azlactone). The azlactone-functional compound had a Brookfield viscosity at 22° C. equal to 30 poises.

EXAMPLES 11-12

Using procedures similar to that of Example 10, except that the reaction mixtures were heated at 50° C. for 18-24 hours, azlactone-functional compounds were prepared from 2-ethenyl-4,4-dimethyl-2-oxazolin-5-one and the following secondary amines:

(a) Jeffamine® CD-230 (Jefferson Chemical Co., Inc., equiv. wt.=172). The azlactone-functional compound was confirmed by spectroscopic analysis and had a Brookfield viscosity at 22° C. equal to 124 poises.

(b) N-(3-isopropyleaminopropyl)methacrylamide (Jefferson Chemical Co., Inc.). The azlactone-functional compound was confirmed by spectroscopic analysis.

EXAMPLES 13-24

In order to assess the effect of steric hindrance on Michael Reaction versus ring-opening reaction, trials were conducted by a procedure similar to that used in Example 11. Ratios of Michael Reaction products (azlactone-functional compounds) to ring-opening products (acrylamidoacylated compounds) were determined by $^1$H-NMR analysis, and the results are given in Table II.

TABLE II

| Examples | Amine | Michael:Ring-opening |
|---|---|---|
| 13 | N—Ethylcyclohexylamine | 100:0 |
| 14 | N—Methylaniline | 100:0 |
| 15 | 2-Methylpiperidine | ≧99:1 |
| 16 | Diisobutylamine | 99:1 |
| 17 | Diethylamine | 93:7 |
| 18 | Di-n-butylamine | 91:9 |
| 19 | N—Methyl-N—benzylamine | 83:17 |
| 20 | Piperidine[a] | 81:19 |
| 21 | 3-Methylaminopropionitrile | 60:40 |
| 22 | N—Methyl-N—butylamine[a] | 49:51 |
| 23 | Pyrrolidine[a] | 16:84 |
| 24 | t-Butylamine | 62:38 |

[a]Reaction mixtures cooled in ice bath until initial exotherm had subsided, then heated at 50° C. until reaction was complete.

The data of Table II show that, under the conditions used, secondary amines and alkenyl azlactones predominantly underwent a Michael Reaction. Example 23, using pyrrolidine, which is an unencumbered secondary amine, predominantly underwent ring-opening.

EXAMPLE 25

Bis(azlactones) were added to various curing agents, the mixtures stirred with a spatula, and the "gel time" noted as the time at which further stirring became impossible. In all cases the ratio of equivalents of the reactable nucleophilic group of the curing agent to equivalents of azlactone groups was approximately 1:1. Results are listed in Table III.

TABLE III

| Bis(azlactone) | Curing agent | Temperatures (°C.) | Gel Time (sec) |
|---|---|---|---|
| Ex. 6 | T-403/TETA[a] | 22 | 90 |
| Ex. 6 | T-403/TETA[a] | 50 | 30 |
| Ex. 6 | Versamide® 140[b] | 22 | 5 |
| Ex. 6 | Glycerol[c] | 22 | 60 |
| Ex. 2 | Emerez® 1514[d] | 22 | 20 |

[a]A 90:10 (equiv./equiv.) mixture of Jeffamine® T-403/triethylenetetramine
[b]Polyamide resin, amine value 385, General Mills, Inc.
[c]BF$_3$ catalyst used
[d]Polyamide resin, amine value 350-400, Emery Industries, Inc.

EXAMPLE 26

The following example illustrates the potential of the azlactone-functional materials of the present invention to be used as components of curable adhesives. Approximately equal parts by volume of the tris(azlactone) of Example 7 and Emerez 1514 were applied to separate specimens of polished maple wood. The two specimens were then joined and pressed together with finger pressure to achieve good contact. Within 30 seconds the bond strength had built to a point where the two specimens could not be pulled apart.

EXAMPLES 27-29

Terpolymers were prepared by copolymerization of various amounts as shown in Table IV of isooctyl acrylate (IOA), N-vinylpyrrolidone (NVP), and 2-hydroxyethyl methacrylate (HEMA) as a 50 percent solution by weight in 65:35 (wt/wt) heptane/acetone as solvent at 55° C. for 24 hours under an inert atmosphere using 0.2 percent by weight azobis(isobutyronitrile) (AIBN) as the free radical initiator. The polymer solutions were diluted to 33 percent solids and a portion of each was knife-coated onto polyester film (0.05 mm) to a thickness of about 0.25 mm and dried in an air-circulating oven at 88° C. for 10 minutes to remove solvent and give a dry coating weight of about 64 g/m$^2$. A second portion of each polymer solution was formulated with enough bis(azlactone) of Example 6 to give a 1:1 molar ratio of azlactone:hydroxyl groups of the acrylate polymer. Just prior to coating, ethanesulfonic acid (1 percent based upon total weight of polymer and bis(azlactone)) was added as a catalyst and coatings were then made as above. Tape cohesive strengths of the resultant pressure sensitive adhesives were compared by means of a standard shear strength test (Interim Federal Test Method Standard No. 147, Mar. 12, 1963), in which a 500 g load was suspended from an adhesive contact area of 6.4 cm² and the time required for the tape to separate from the steel plate was measured and recorded in minutes as the average of three trials. The results are shown in Table IV.

TABLE IV

| | Terpolymer (Parts by wt.) | | | Shear (min) | |
|---|---|---|---|---|---|
| Example | IOA | NVP | HEMA | original | bis(azlactone) crosslinked |
| 27 | 90.5 | 9 | 0.5 | 1.6 | 20.8 |
| 28 | 90 | 9 | 1.0 | 20.7 | 35.2 |
| 29 | 88 | 9 | 2.0 | 36.8 | 107.2 |

The data of Table IV show the utility of the compositions of the present invention as crosslinking agents under mild conditions.

EXAMPLE 30

The following example illustrates the use of liquid azlactone-functional materials of the instant invention for the reaction injection molding (RIM) of plastic parts. The Flexamatic HP-6A laboratory RIM unit (Martin Sweets Company) was utilized. Resin part A consisted of the bis(azlactone) of Example 6, viscosity at 40° C. which equaled 245 cps. Resin part B was prepared by mixing Versamid ® 140, Jeffamine ® T-403, and triethylenetetramine in a 1:0.9:0.1 ratio (based on amine equivalent weight) and had a Brookfield viscosity at 40° C. which equaled 255 cps. Mixing equivalent amounts of part A and part B at 40° C. gave a gel time of approximately 15 seconds. Parts A and B were loaded into the appropriate feed tanks of the RIM unit, preequilibrated to 40° C., then injected into a 1 cm×8 cm×16 cm steel mold at a mixing ratio of 1.2:1 A/B (by volume) to give a tough molded specimen with excellent overall appearance.

Various modifications and alterations of this invention will become apparent to those skilled in the art without departing from the scope and spirit of this invention, and it should be understood that this invention is not to be unduly limited to the illustrative embodiments set forth herein.

We claim:
1. A method for preparing a polyamide resin comprising the steps of:
(1) admixing, in the absence of solvent, 0.8 to 1.2 equivalents of
 (a) an azlactone-functional compound having the formula

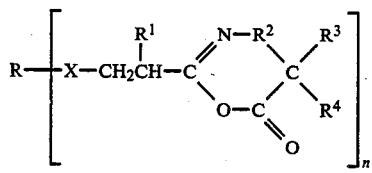

Formula I wherein
$R^1$ is hydrogen, chlorine or a methyl group;
$R^2$ is a single bond or a methylene or ethylene group, the last two of which can be substituted by alkyl groups having 1 to 6 carbon atoms or phenyl groups;
$R^3$ and $R^4$ are independently an alkyl or cycloalkyl group having up to 12 carbon atoms, an aryl or aralkyl group having 6 to 12 carbon atoms, or $R^3$ and $R^4$ taken together with the carbon atom to which they are attached form a 5- to 12-membered carbocyclic ring;
X is a nucleophilic group selected from

and —S—, is which $R^5$ is a hydrocarbyl group selected from (1) an alkyl or cycloalkyl group having up to 18 carbon atoms and (2) an aryl or aralkyl group having 6 to 12 carbon atoms;
R is a mono or polyvalent organic group that has a valence of n and is the residue of a nucleophilic group-substituted compound, $(HX)_nR$, in which X is defined above, the residue having a molecular weight up to 20,000, R being selected from (1) an aliphatic group having 2 to 20 carbon atoms and an aryl group having up to 20 carbon atoms, these groups optionally having one to four catenary heteroatoms of oxygen, nitrogen or sulfur, (2) polyoxyalkylene, (3) polyester, (4) polyolefin, (5) polyacrylate, and (6) polysiloxane, all optionally including at least one non-nucleophilic or nucleophilic group, and
n is an integer having a value of one to six, and
(b) one equivalent of at least one nucleophilic group-functional compound

wherein
$R^6$ is an organic group that has a valence of m and is the residue of a nucleophilic group-substituted compound $R^6(YH)_m$, $R^6$ being selected from
 (1) mono- and polyvalent aliphatic and aromatic groups having 2 to 20 carbon atoms and optionally one to four catenary heteroatoms selected from oxygen, nitrogen, and sulfur,
 (2) mono- and polyvalent groups selected from polyoxyalkylene, polyester, polyolefin, polyacrylate, and polysiloxane having a molecular weight up to 500,000,
both (a) and (b) groups optionally substituted by at least one non-nucleophilic group or atom selected from cyano, halo, ester, ether, keto, nitro, silyl, and sulfide, wherein
Y is —O—, or

in which $R^7$ is hydrogen or a lower alkyl group of one to four carbon atoms, and
m is an integer having a value of 1 to 20,000;
(2) allowing the mixture to react at 0° C. to 300° C.
2. The method according to claim 1 wherein in said azlactone-functional compound $R^5$ is substituted by at least one ether, keto, or ester group having 1 to 10 carbon atoms, a cyano or silyl group, or a sulfide or halo atoms.

3. A polyamide resin having repeating units having the structure

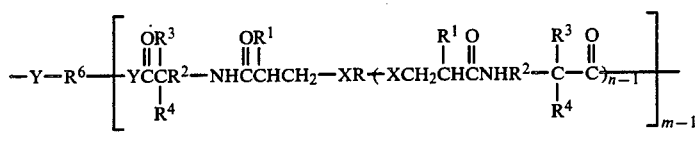

Formula IV

wherein
R¹ is hydrogen, chlorine or a methyl group;
R² is a single bond or a methylene or ethylene group, the last two of which can be substituted by alkyl groups having 1 to 6 carbon atoms or phenyl groups;
R³ and R⁴ are independently an alkyl or cyclo-alkyl group having 1 to 12 carbon atoms, an aryl or aralkyl group having 6 to 12 carbon atoms, or R³ and R⁴ taken together with the carbon atom to which they are attached form a 5- to 12-membered carbocyclic ring;
X is a nucleophilic group selected from

and —S—, in which $R^5$ is a hydrocarbyl group selected from (1) an alkyl or cycloalkyl group having 1 to 18 carbon atoms, optionally substituted by at least one cyano, halo, ether, keto, ester, silyl, or sulfide group or atom having 1 to 10 carbon atoms or (2) an aryl or aralkyl group having 6 to 12 carbon atoms optionally substituted by at least one cyano, halo, ether, keto, ester, silyl, or sulfide group or atom having 1 to 10 carbon atoms;
R is a organic group that has valence of n and is the residue of a nucleophilic group-substituted compound, $(HX)_nR$, in which X is defined above, the residue having a molecular weight up to 20,000, R being selected from (1) an aliphatic group having 2 to 20 carbon atoms, these groups optionally having one to four catenary heteroatoms of oxygen, nitrogen or sulfur, (2) polyoxyalkylene, (3) polyester, (4) polyolefin, (5) polyacrylate; and (6) polysiloxane, species 1 to 6 all optionally including at least one non-nucleophilic or nucleophilic group,
R⁶ is an organic group that has a valence of m and is the residue of a nucleophilic group-substituted compound $R^6(HY)_m$, R⁶ being selected from
(a) mono- and polyvalent aliphatic and aromatic groups having 2 to 20 carbon atoms and optionally one to four catenary heteroatoms selected from oxygen, nitrogen, and sulfur,
(b) mono- and polyvalent groups selected from polyoxyalkylene, polyester, polyolefin, polyacrylate, and polysiloxane having a molecular weight up to 500,000,
both (a) and (b) groups being optionally substituted by at least one non-nucleophilic group or atom selected from cyano, halo, ester, ether, keto, nitro, silyl, and sulfide, wherein
Y is —O—, —X—, or

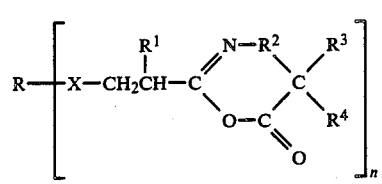

in which R⁷ is hydrogen or lower alkyl group having one to four carbon atoms, and
m is an integer of 1 to 20,000 and
n is an integer having a value of one to six.

4. The polyamide resin according to claim 3 wherein $R^6(YH)_m$ is N,N'-bis(3-aminopropyl)piperazine, polyoxyalkylene polyamine, or triethylenetetraamine.

5. The polyamide resin according to claim 3 wherein m=2 and n=2.

6. A compositions of matter comprising
(a) in the range of 0.8 to 1.2 equivalents of an azlactone-functional compound having the formula Formula I

wherein
R¹ is hydrogen, chlorine or a methyl group;
R² is a single bond or a methylene or ethylene group, the last two of which can be substituted by alkyl groups having 1 to 6 carbon atoms or phenyl groups;
R³ and R⁴ are independently an alkyl or cycloalkyl group having up to 12 carbon atoms, an aryl or aralkyl group having 6 to 12 carbon atoms, or R³ and R⁴ taken together with the carbon atom to which they are attached form a 5- to 12-membered carbocyclic ring;
X is a nucleophilic group selected from $$\begin{array}{c} R^5 \\ | \\ -N- \end{array}$$

and —S—, in which R⁵ is a hydrocarbyl group selected from (1) an alkyl or cycloalkyl group having up to 18 carbon atoms and (2) an aryl or aralkyl group having 6 to 12 carbon atoms;
R is a mono or polyvalent organic group that has a valence of n and is the residue of a nucleophilic group-substituted compound, $(HX)_nR$, in which X is defined above, the residue having a molecular weight up to 20,000, R being selected from (1) an aliphatic group hav-ng 2 to 20 carbon atoms and an aryl group having up to 20 carbon atoms, these groups optionally having one to four catenary heteroatoms of oxygen, nitrogen or sulfur, (2) polyoxyalkylene, (3) polyester, (4) polyolefin, (5) polyacrylate, and (6) polysiloxane, all optionally including at least one non-nucleophilic or nucleophilic group, and n is an integer having a value of one to six, and (b) one equivalent of at least one nucleophilic group-functional compound.

7. The composition of matter according to claim 6 wherein $R^5$ is substituted by at least one ether, keto, or ester group having 1 to 10 carbon atoms, a cyano or silyl group, or a sulfide or halo atom.

8. The composition of matter according to claim 6 wherein said nucleophilic group-functional compound of paragraph (b) is an alcohol, or an amine.

9. A two-part composition disposed in a single unitary package with the parts of the composition stored in separate compartments within the package and adapted upon mixing, without solvent, for use as an adhesive, the composition comprising:

(1) in one part:
0.8 to 1.2 equivalents of an azlactone-functional compound having the formula

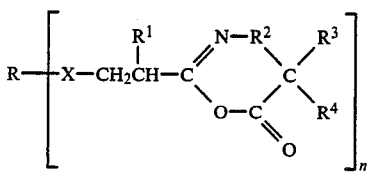

Formula I wherein $R^1$ is hydrogen, chlorine or a methyl group;

$R^2$ is a single bond or a methylene or ethylene group, the last two of which can be substituted by alkyl groups having 1 to 6 carbon atoms or phenyl groups;

$R^3$ and $R^4$ are independently an alkyl or cycloalkyl group having up to 12 carbon atoms, an aryl or aralkyl group having 6 to 12 carbon atoms, or $R^3$ and $R^4$ taken together with the carbon atom to which they are attached form a 5- to 12-membered carbocyclic ring;

X is a nucleophilic group selected from

and —S—, in which $R^5$ is a hydrocarbyl group selected from (1) and alkyl or cycloalkyl group having up to 18 carbon atoms and (2) an aryl or aralkyl group having 6 to 12 carbon atoms;

R is a mono or polyvalent organic group that has a valence of n and is the residue of a nucleophilic group-substituted compound, $(HX)_nR$, in which X is defined above, the residue having a molecular weight up to 20,000, R being selected from (1) an aliphatic group having 2 to 20 carbon atoms and an aryl group having up to 20 carbon atoms, these groups optionally having one to four catenary heteroatoms of oxygen, nitrogen or sulfur, (2) polyoxyalkylene, (3) polyester (4), polyolefin, (5) polyacrylate, and (6) polysiloxane, all optionally including at least one non-nucleophilic or nucleophilic group, and n is an integer having a value of one to six, and (2) in a second part:
one equivalent of a nucleophilic group-functional compound, $R^6(YH)_m$; wherein $R^6$ is an organic group that has a valence of m and is the residue of a nucleophilic group-substituted compound, $R^6(YH)_m$, $R^6$ being selected from
(a) mono- and polyvalent aliphatic and aromatic groups having 2 to 20 carbon atoms and optionally one to four catenary heteroatoms selected from oxygen, nitrogen, and sulfur,
(b) mono- and polyvalent groups selected from polyoxyalkylene, polyester, polyolefin, polyacrylate, and polysiloxane having a molecular weight up to 500,000, both (a) and (b) groups being optionally substituted by at least one non-nucleophilic group or atom selected from cyano, halo, ester, ether, keto, nitro, silyl, and sulfide, wherein Y is —O—, —X—, or

in which $R^7$ is hydrogen or a lower alkyl group of one to four carbon atoms, and m is an integer of 1 to 20,000.

10. The composition of matter according to claim 9 wherein $R^5$ is substituted by at least one ether, keto, or ester group having 1 to 10 carbon atoms, a cyano or silyl group, or a sulfide or halo atom.

11. A process for adhering two substrates together comprising the steps:

(1) providing two substrates,
(2) coating, without solvent, upon one surface of one substrate a layer of the azlactone-functional compound having the formula

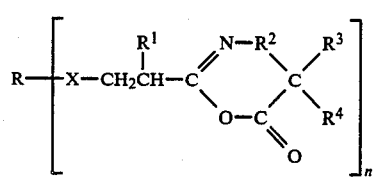

Formula I wherein $R^1$ is hydrogen, chlorine or a methyl group;

$R^2$ is a single bond of a methylene or ethylene group, the last two of which can be substituted by alkyl groups having 1 to 6 carbon atoms or phenyl groups;

$R^3$ and $R^4$ are independently an alkyl or cycloalkyl group having up to 12 carbon atoms, an aryl or aralkyl group having 6 to 12 carbon atoms, or $R^3$ and $R^4$ taken together with the carbon atom to which they are attached form a 5- to 12-membered carbocyclic ring;

X is a nucleophilic group selected from

and —S—, in which $R^5$ is a hydrocarbyl group selected from (1) an alkyl or cycloalkyl group having up to 18 carbon atoms and (2) an aryl or aralkyl group having 6 to 12 carbon atoms;

R is a mono or polyvalent organic group that has a valence of n and is the residue of a nucleophilic group-substituted compound, $(HX)_nR$, in which X is defined above, the residue having a molecular weight up to 20,000, R being selected from (1) an aliphatic group having 2 to 20 carbon atoms, these groups optionally having one to four catenary heteroatoms of oxygen, nitrogen or sulfur, (2) polyoxyalkylene, (3) polyester, (4) polyolefin, (5) polyacrylate, and (6) polysiloxane, all optionally including at least one non-nucleophilic or nucleophilic group, and n is an integer having a value of one to six, and (3) coating, without solvent, upon one surface of said second substrate a layer of at least one nucleophilic group-substituted compound, $R^6(YH)_m$, wherein $R^6$ is an organic group that has a valence of m and is the residue of a nucleophilic group-substituted compound, $R^6(YH)_m$, $R^6$ being selected from (a) mono- and polyvalent aliphatic and aromatic groups having 2 to 20 carbon atoms and optionally one to four caternary heteroatoms selected from oxygen, nitrogen, and sulfur, (b) mono- and polyvalent groups selected from polyoxyalkylene, polyester, polyolefin, polyacrylate, and polysiloxane having a molecular weight up to 500,000, both (a) and (b) groups being optionally substituted by at least one non-nucleophilic group or atom selected from cyano, halo, ester, ether, keto, nitro, silyl, and sulfide, wherein Y is —O—, —X—, or

in which $R^7$ is hydrogen or a lower alkyl group of one to four carbon atoms, and m is an integer having a value of 1 to 20,000, (4) pressing the coated surfaces of the substrates together, and (5) allowing said at least one nucleophilic compound to cure said azlatone-functional compound.

12. The method according to claim 11 wherein in said azlactone-functional compound $R^5$ is substituted by at least one ether, keto, or ester group having 1 to 10 carbon atoms, a cyano or silyl group, or a sulfide or halo atom.

13. A process for adhering two substrates together comprising the steps:

(1) providing two substrates, (2) admixing, in the absence of solvent, 0.8 to 1.2 equivalents of an azlactone-functional compound having the formula

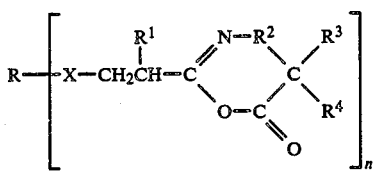

Formula I wherein $R^1$ is hydrogen, chlorine or a methyl group;

$R^2$ is a single bond or a methylene or ethylene group, the last two of which can be substituted by alkyl groups having 1 to 6 carbon atoms or phenyl groups;

$R^3$ and $R^4$ are independently an alkyl or cycloalkyl group having up to 12 carbon atoms, an aryl or aralkyl group having 6 to 12 carbon atoms, or $R^3$ and $R^4$ taken together with the carbon atom to which they are attached form a 5- to 12-membered carbocyclic ring;

X is nucleophilic group selected from

and —S—, in which $R^5$ is a hydrocarbyl group selected from (1) an alkyl or cycloalkyl group having up to 18 carbon atoms and (2) an aryl or aralkyl group having 6 to 12 carbon atoms;

R is a mono or polyvalent organic group that has a valence of n and is the residue of a nucleophilic group-substituted compound, $(HX)_nR$, in which X is defined above, the residue having a molecular weight up to 20,000, R being selected from (1) an aliphatic group having 2 to 20 carbon atoms, these groups optionally having one to four catenary heteroatoms of oxygen, nitrogen or sulfur, (2) polyoxyalkylene, (3) polyester, (4) polyolefin, (5) polyacrylate, and (6) polysiloxane, all optionally including at least one non-nucleophilic or nucleophilic group, and n is an integer having a value of one to six, with one equivalent of a nucleophilic group-functional compound, $R^6(YH)_m$, wherein $R^6$ is an organic group that has a valence of m and is the residue of a nucleophilic group-substituted compound, $R^6(YH)_m$, $R^6$ being selected from (a) mono- and polyvalent aliphatic and aromatic groups having 2 to 20 carbon atoms and optionally one to four catenary heteroatoms selected from oxygen, nitrogen, and sulfur, (b) mono- and polyvalent groups selected from polyoxyalkylene, polyester, polyolefin, polyacrylate, and polysiloxane having a molecular weight up to 500,000, both (a) and (b) groups being optionally substituted by at least one non-nucleophilic group or atom selected from cyano, halo, ester, ether, keto, nitro, silyl, and sulfide, wherein Y is —O—, —X—, or

in which $R^7$ is hydrogen or a lower alkyl group of one to four carbon atoms, and m is an integer having a value of 1 to 20,000, (3) applying said admixture to one surface of either or both of said substrates, (4) pressing the surfaces together into adhesive contact, and (5) allowing said admixture to cure.

14. The method according to claim 13 wherein in said azlactone-functional compound $R^5$ is substituted by at least one ether, keto, or ester group having 1 to 10 carbon atoms, a cyano or silyl group, or a sulfide or halo atom.

* * * * *